United States Patent
Wilks et al.

(10) Patent No.: US 6,825,387 B2
(45) Date of Patent: Nov. 30, 2004

(54) LOW SODIUM CLEAVAGE PRODUCT

(75) Inventors: Theodor Robert Wilks, Sugar Land, TX (US); Mark Thornton Vandersall, Jamison, PA (US); William Frederick Rogers, Jr., Seabrook, TX (US)

(73) Assignee: Kellogg Brown & Root, Inc., Houston, TX (US)

( * ) Notice: Subject to any disclaimer, the term of this patent is extended or adjusted under 35 U.S.C. 154(b) by 0 days.

(21) Appl. No.: 10/605,155

(22) Filed: Sep. 11, 2003

(65) Prior Publication Data

US 2004/0106831 A1 Jun. 3, 2004

Related U.S. Application Data

(60) Provisional application No. 60/319,619, filed on Oct. 15, 2002.

(51) Int. Cl.⁷ .............................................. C07C 37/08
(52) U.S. Cl. ....................................... 568/798; 568/754
(58) Field of Search ................................. 568/798, 754

(56) References Cited

U.S. PATENT DOCUMENTS

| | | | | |
|---|---|---|---|---|
| 2,734,085 A | | 2/1956 | Adams et al. ............. 260/593 |
| 2,737,480 A | | 3/1956 | Adams et al. ............. 202/39 |
| 2,744,143 A | | 5/1956 | Filar ........................ 568/798 |
| 2,757,209 A | * | 7/1956 | Joris ........................ 568/754 |
| 3,931,339 A | | 1/1976 | Cooke ..................... 568/754 |
| 4,262,150 A | | 4/1981 | Pujado .................... 568/754 |
| 4,262,151 A | | 4/1981 | Pujado .................... 568/754 |
| 4,358,618 A | * | 11/1982 | Sifniades et al. ......... 568/385 |
| 4,568,466 A | | 2/1986 | Salem et al. ............. 210/663 |
| 4,626,600 A | | 12/1986 | Fulmer et al. ........... 568/411 |
| 4,747,954 A | | 5/1988 | Vaughn et al. .......... 210/670 |
| 5,245,090 A | | 9/1993 | DeCaria et al. ......... 568/798 |
| 5,304,684 A | | 4/1994 | Nishida et al. .......... 568/385 |
| 5,510,543 A | | 4/1996 | Fulmer et al. ........... 568/754 |
| 6,066,767 A | | 5/2000 | Zakoshansky et al. ... 568/749 |
| 6,635,789 B2 | * | 10/2003 | Fulmer et al. ........... 568/754 |
| 2002/0040165 A1 | * | 4/2002 | Hertzog et al. ......... 568/383 |
| 2003/0088129 A1 | * | 5/2003 | Marshall et al. ........ 568/385 |

FOREIGN PATENT DOCUMENTS

| | | | |
|---|---|---|---|
| DE | 1239701 | | 5/1967 |
| EP | 1018501 | | 7/2000 |
| GB | 743004 | | 1/1956 |
| GB | 970945 | | 9/1964 |
| GB | 1108233 A | * | 4/1968 |

* cited by examiner

*Primary Examiner*—Michael L. Shippen
(74) *Attorney, Agent, or Firm*—Kellogg Brown & Root, Inc.

(57) ABSTRACT

Washed cleavage product (WCP) in a phenol manufacturing process is treated to remove sodium ions. The WCP is contacted with a cation exchange resin in hydrogen form, and then with anion exchange resin in free base or hydroxide form, to produce a WCP essentially free of sodium ions. The cation and anion exchange resins are regenerated with acid and caustic, respectively. The treatment improves productivity and product quality of new and existing phenol processes.

25 Claims, 4 Drawing Sheets

LOW SODIUM CLEAVAGE PRODUCT

BACKGROUND OF INVENTION

This invention relates to phenol and acetone production, particularly to removing salts from washed cleavage product from the reaction of cumene hydroperoxide with an acid catalyst, and to a low sodium washed cleavage product.

Sodium is a constituent of reagents commonly used in manufacturing phenol. Other metals may appear in place of or in addition to sodium. In product recovery aspects of phenol processes, metal salt constituents can hinder process efficiency and will contaminate process byproducts. Removing metals in selected aspects of the phenol process can improve process efficiencies and reduce the production of problematic byproducts.

Phenol can be produced from oxidation of cumene to cumene hydroperoxide, followed by acid catalyzed decomposition to a cleavage product comprising solutions of phenol, acetone, and byproducts that include organic acids. The decomposition is commonly called cleavage. Cleavage product is treated with alkaline wash solutions to remove acid catalyst and a portion of the organic acid byproducts. After washing, the cleavage product and wash solutions can contain salts predominantly including sodium hydroxide (NaOH), sodium bisulfate ($NaHSO_4$), sodium sulfate ($Na_2SO_4$), sodium phenate ($NaOC_6H_5$), sodium carbonate ($Na_2CO_3$), sodium bicarbonate ($NaHCO_3$) and sodium salts of organic acids such as formic, acetic, benzoic, propionic, and oxalic acids in various combinations. Washed cleavage product (WCP) is separated from the wash solutions and refined in recovery operations entailing distillation and separation to recover products acetone and phenol, unreacted cumene, and alpha-methylstyrene (AMS). Recovery also purges low-boiling and high-boiling byproduct impurities.

Residual salts entering the recovery operations as constituents in the washed cleavage product can result in fouling of separation and heat exchange equipment. Fouling can be delayed or slowed by operating recovery processes at reduced efficiencies. Ultimately, heavy organic waste products from the phenol process contain concentrations of salts that can present a disposal problem for the heavy organic impurities that might, for example, otherwise be burned as waste fuel.

Representative phenol manufacturing methods using various alkaline solutions to wash cleavage product are described in U.S. Pat. Nos. 2,734,085; 2,737,480; 2,744,143; 3,931,339; 4,262,150; 4,262,151; 4,626,600; 5,245,090 5,304,684; 5,510,543; 6,066,767. U.S. Pat. No. 4,568,466 to Salem et al discloses ion exchange applications to high-purity boiler feed waters. U.S. Pat. No. 4,747,954 to Vaughn et al. teaches formulations of ion exchange resins. All of these patents are hereby incorporated by reference herein in their entirety.

There is a need in the field of manufacturing phenol and acetone for improvements to benefit the efficiency and economics of production, particularly regarding productivity, recovery operations, and waste disposal. It would be desirable to improve the production of phenol and acetone in ways that (1) increase product recovery and plant availability, (2) reduce waste generation, (3) divert salt constituents out of process subsystems that incur operating and maintenance costs when elevated salt levels are characteristically present, (4) separate salt constituents from organic byproduct and waste streams to facilitate more cost effective disposal of the organics, and (5) facilitate greater internal recycle of recoverable intermediate byproducts and unused reagent, thereby reducing costs of makeup reagents.

SUMMARY OF INVENTION

The present invention removes cations and anions from washed cleavage product from the reaction of cumene hydroperoxide with an acid catalyst. The method contemplates using an alkaline washing operation to neutralize the acid and remove the bulk of the ions from the cleavage product. The washed cleavage product is then passed through cation and anion exchangers to remove the ions prior to distillation or other processing to recover acetone, phenol and other compounds from the cleavage product. The ion removal greatly reduces fouling in the product recovery, with less waste disposal, less operating downtime and longer operation between maintenance cycles, better heat transfer and energy efficiency, higher production rates, and the like.

In one aspect, the invention provides a process for reducing ion content of washed cleavage product from the reaction of cumene hydroperoxide with an acid catalyst. The process includes contacting the washed cleavage product with a cation exchanger to remove positively charged ions including sodium, contacting the washed cleavage product with an anion exchanger to remove negatively charged ions including sulfate, and recovering exchanger effluent lean in sodium and sulfate. The washed cleavage product supplied to the exchangers can be whole washed cleavage product, or dewatered cleavage product, e.g. obtained by coalescing the whole washed cleavage product. The washed cleavage product preferably comprises a molar ratio of acetone to phenol from 0.8 to 1.5, from 2 to 30 weight percent cumene, from 4 to 20 weight percent water, and from 10 to 400 ppmw sodium, more preferably less than 300 ppmw sodium and especially less than 200 ppmw sodium. The exchanger effluent preferably has less than 10 ppmw sodium, more preferably less than 5 ppmw, and especially less than 2 ppmw sodium.

The cation exchanger is preferably a strong acid cation exchange resin in hydrogen form, or a weak acid cation exchange resin in hydrogen form. The anion exchanger is preferably a weak base anion exchange resin in free base form, or a strong base anion exchange resin in hydroxide form. The ion exchangers can be a mixed bed of exchanger media comprising both cation and anion exchangers, preferably with an effluent having a sodium concentration less than 5 ppmw. In another embodiment, the anion and cation exchangers comprise serial beds of anion and cation exchange resins, respectively, preferably with an effluent having a sodium concentration less than 10 ppmw and a pH from 3.5 to 6.0.

The process preferably includes a cation exchange adsorption cycle at a temperature from 20° to 80° C. and a feed rate to the cation exchange resin bed from 1 to 60 cubic meters per cubic meter of bed volume per hour (BV/hr). A cation exchange regeneration cycle preferably employs from 0.5 to 10 weight percent aqueous sulfuric acid. The process preferably includes an anion exchange adsorption cycle at a temperature from 20° to 80° C. and a feed rate to the anion exchange resin bed from 1 to 60 BV/hr. An anion exchange regeneration cycle can employ aqueous NaOH, sodium phenate, or a combination thereof, at NaOH or NaOH-equivalent concentration from 0.2 to 8 weight percent.

In another embodiment, the present invention provides a process for producing phenol that includes oxidizing cumene to cumene hydroperoxide, cleaving the cumene hydroperoxide in the presence of an acid catalyst to form a cleavage product mixture including phenol and acetone, washing the cleavage product mixture with alkaline wash solution to form a washed cleavage product, contacting the washed cleavage product with a cation exchanger and an anion exchanger to form a polished cleavage product of reduced ion content, preferably as described above, and recovering phenol and acetone from the polished cleavage product. The washing can include coalescing a whole washed cleavage product to separate an aqueous phase and recover the washed cleavage product for the exchanger contacting, wherein the recovered washed cleavage product comprises a molar ratio of acetone to phenol from 0.8 to 1.5, from 2 to 30 weight percent cumene, from 4 to 20 weight percent water, and from 10 to 400 ppmw sodium, more preferably less than 300 ppmw sodium and especially less than 200 ppmw sodium.

The product recovery can include distillation of the polished cleavage product and recovery of an aqueous stream recycled to the washing step. The process can also include dephenolating spent wash water from the washing. The dephenolation can include acidifying the spent wash water and extracting phenol from the acidified wash water with an immiscible solvent obtained from the phenol and acetone recovery, and recycling the extract to the cleavage product in the washing. The process can further include regenerating the cation and anion exchanger with aqueous and organic fluids, recycling spent aqueous fluid to the dephenolation, and recycling spent organic fluid to the washing.

DETAILED DESCRIPTION

Figure 1:
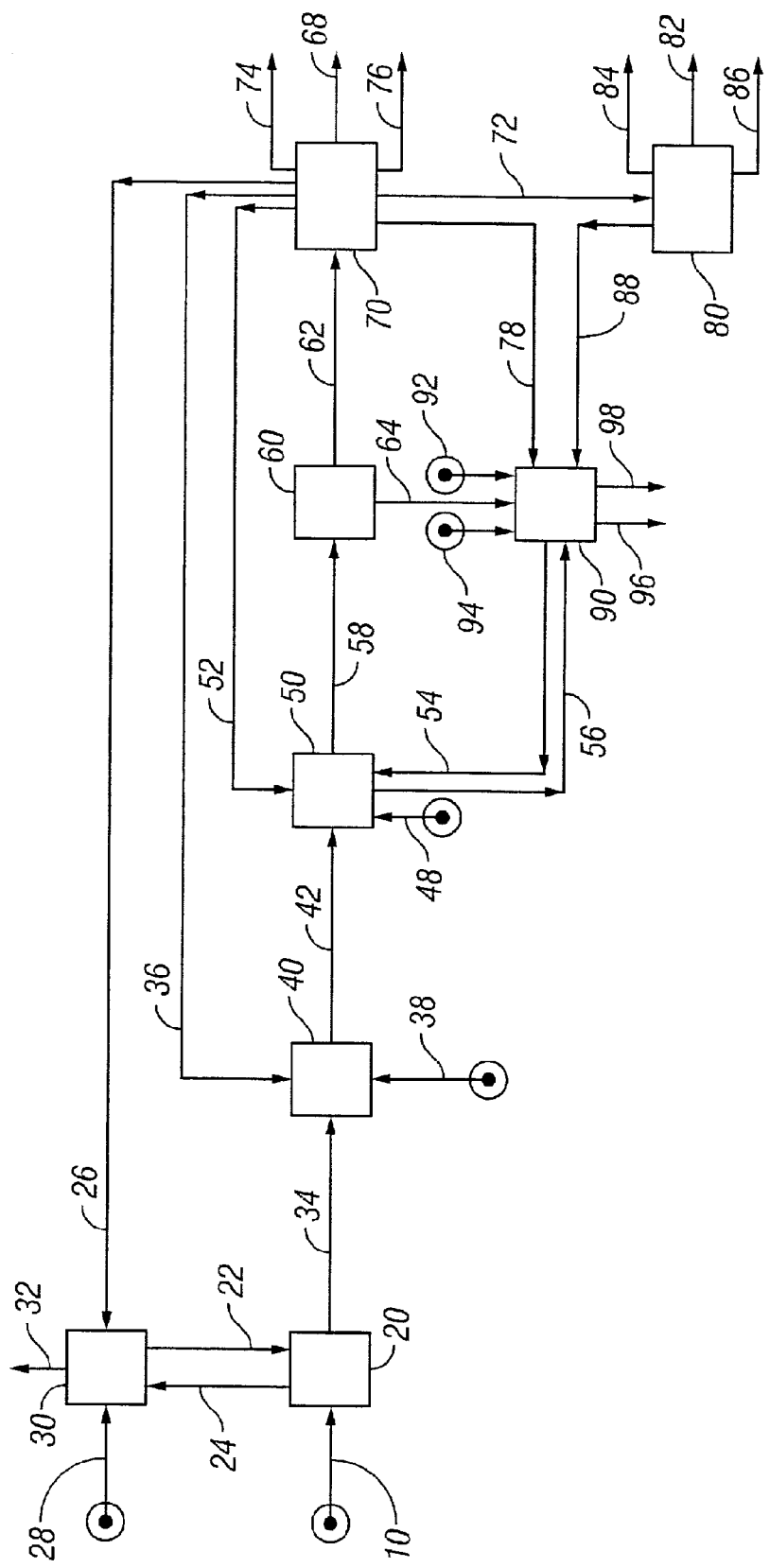
FIG. 1 is a simplified process diagram for the manufacture of phenol according to one embodiment of the invention.

FIG. 1 illustrates a process for manufacturing phenol from cumene stream (10), including cumene hydroperoxide concentrator (20), cumene oxidizer (30) to cumene hydroperoxide, cumene hydroperoxide cleavage (40) to a mixture of phenol and acetone, washing (50) with one or more alkaline solutions, ion exchange (60) to remove salts, acetone recovery (70), phenol distillation (80), and wastewater dephenolation (90).

Feed cumene stream (10) and product stream (22) from the oxidizer (30) are introduced into conventional concentrator (20). The concentrator (20) supplies feed cumene (10), together with any cumene recovered from the oxidizer product stream (22), as a combined cumene stream (24) to the conventional oxidizer (30). A recycle cumene stream (26) is supplied to the oxidizer (30) from downstream acetone recovery (70), discussed below. Air (28) is introduced to the oxidizer (30) to partially oxidize the cumene to cumene hydroperoxide (CHP) in a well known manner. The byproduct dimethylbenzyl alcohol (DMBA) is also formed to a lesser extent, as well as acetophenone (AP), and other oxidation byproducts. Spent air (32) is exhausted from the oxidizer (30). The oxidizer product stream (22), including the CHP, DMBA, AP, and unreacted cumene, is supplied to the concentrator (20) as previously mentioned, where unreacted cumene is recovered for recycle to the oxidizer (30).

The effluent in concentrator product stream (34) is rich in CHP for feed to cleavage reactor (40). A stream (36) typically recycles acetone from downstream acetone recovery (70), discussed below. A catalyst stream (38), commonly sulfuric acid, is supplied to the cleavage reactor (40) to facilitate the CHP cleavage to form a product mixture (42) with phenol and acetone as the principal products, along with unreacted AP and cleavage byproducts comprising alpha-methyl styrene (AMS), cumyl phenol, and other organic acids.

The product mixture (42) flows to washing (50) to be contacted with one or more alkaline wash solutions (48), typically aqueous NaOH, in a manner well known in the art. An alkaline recycle stream (52) containing phenate from downstream acetone recovery (70) and a second phenate-containing stream (54) from wastewater dephenolation (90) are also fed to the washing system (50) to reduce the makeup alkaline solution requirements and minimize phenol losses.

The alkaline washing results in an aqueous phase of spent wash (56) and a washed cleavage product (WCP) (58) as an organic phase. The alkaline wash neutralizes and extracts a major portion of the acid catalyst and salt components from the product phase, including mineral and organic acids. The product phase retains minor portions of acid catalyst, sodium cations, and salt anions, and a minor proportion of water. The spent wash (56) typically comprises from 85 to 95 weight percent of the alkaline solution feed streams (48), (52), (54). The whole WCP phase typically comprises at least 75 weight percent of organic compounds, but can include up to 25 weight percent of wash solution dispersed in the WCP. A preferred step in the present invention includes dewatering the whole WCP using conventional coalescing equipment and methodologies to further separate the residual wash solution from the WCP. This can help reduce energy use and flow volume in downstream product recovery by reducing the aqueous content of the WCP (58) to from 85 to 95 weight percent. Water from the coalescing step is discharged with the spent wash (56).

WCP (58) is introduced to ion exchange unit (60) to remove sodium cations and salt-forming anions that can include sulfate, bisulfate, carbonate, bicarbonate, phenates, and other organic acid radicals, as discussed in more detail below. Ion exchange preferably removes from 50 to 98 percent of the sodium and produces a polished WCP (62) with less than 10 ppmw sodium, more preferably less than 5 ppmw, and especially less than 2 ppmw sodium. Thus, a typical sodium content of 30 to 40 ppmw in the prior art WCP can be reduced to less than 5 ppmw. Ion exchangers have finite unit mass capacity for adsorption and are typically rotated through successive, repeating cycles of adsorption operation, regeneration, and standby. Parallel ion exchange trains can be installed to permit continuous processing, such that saturated ion exchange modules undergo regeneration off-line while regenerated modules continue in service. A wastewater stream (64) produced during regeneration of the ion exchange resins is preferably treated in dephenolation unit (90). The water for regeneration is preferably obtained from vacuum towers elsewhere in the facility, e.g. jet condensate, which is sodium free. Caustic for regeneration of cation exchanger can be supplied from stream 48 and/or phenate recycle stream 54 described below.

Polished WCP (62) is fed to acetone fractionation unit (70), which primarily produces a purified acetone product

(68) and a crude phenol product (72), plus light and heavy organic byproduct streams, (74) and (76), respectively. Acetone fractionation (70) also recovers the cumene recycle stream (26), the acetone recycle stream (36), and recycle aqueous stream (52), previously mentioned. Recovered water is sent to the dephenolation unit (90) via line (78). The crude phenol (72) in the prior art without ion exchange polishing would typically have a sodium content of 100–120 ppmw, but this can be as low as about 15 ppmw in the present invention. Another benefit in the acetone fractionation (70) is that the lower sodium content of the polished WCP reduces the frequency of acetone column washings from several times a year, when the sodium in the WCP feed to the column is more than 30 ppmw, to more than a year using the principles of the present invention. The significance of this surprising result is that the acetone fractionation unit (70) can be washed during scheduled plant maintenance shutdowns, instead of shutting down the plant frequently due to the need to wash the acetone distillation column.

The crude phenol product (72) is forwarded to a phenol fractionation unit (80), which primarily produces a purified phenol product (82), plus second light and second heavy organic byproduct streams (84) and (86), respectively. In the prior art the crude heavy byproducts from the phenol recovery might have a typical sodium content of 200–300 ppmw and 2000–2500 in the concentrated heavy byproducts, whereas with the present invention the sodium content could be 30 ppmw and 300 ppmw in the crude and concentrated heavy byproducts, respectively. This is a significant improvement because byproducts of up to 500 ppmw sodium can be easily burned as a fuel, whereas more than 500 ppmw usually requires special treatment for ash handling, and more than 2000–2500 ppmw usually requires costly disposal by incineration.

Phenol fractionation (80) also recovers an intermediate solvent stream (88) used in dephenolation (90). Acetone fractionation (70) and phenol fractionation (80) are more or less conventional, but the benefits of reduced sodium and other ion contents in the polished WCP (62) and crude phenol product (72) can include more efficient operation and longer operation between maintenance shutdowns due to less fouling; less waste disposal; and the like.

The spent wash (56) is a primary wastewater feed to dephenolation (90), which is conventional except that a slightly larger unit than normal may be required to process wastewater (64) generated during aqueous regeneration of the ion exchange resins in unit (60). The spent wash (58) is acidified with acid (92) to convert phenate to phenol, and contacted with the solvent (88) from phenol fractionation to extract phenol from the spent wash (58) according to a well known procedure. The solvent is recovered and dosed with caustic (94), which converts phenol to phenate and allows the phenate to preferentially distribute in an aqueous phase that is recycled as stream (54) to the washing (50). After giving up phenol to the solvent, the dephenolated wash water leaves dephenolation (90) as wastewater (96). Spent solvent (98) from dephenolation (90) is directed to acetone fractionation (70) for recovery of cumene and AMS.

The method of the present invention can be used in a new acetone-phenol plant, and it can also be implemented in existing plants by retrofit. Incorporating ion exchange into an existing phenol plant can facilitate the ability of the existing plant to concentrate and separate products, while avoiding collateral costs for maintenance and waste disposal that would otherwise occur for similar production increase without reduction in salt loadings in the WCP achieved with ion exchange.

Figure 2:
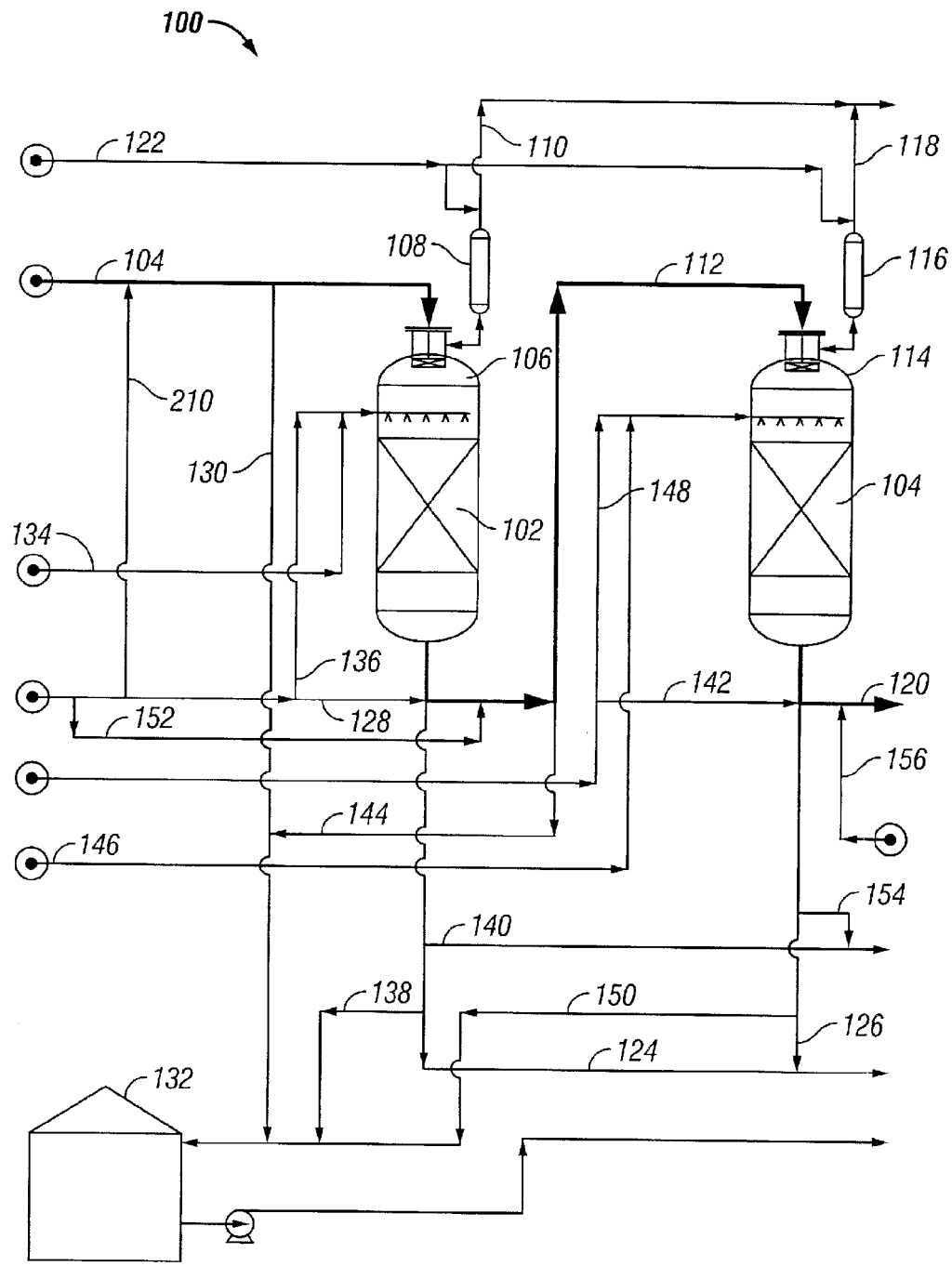
FIG. 2 is a simplified process schematic of one embodiment of sodium removal from washed cleavage product by cation/anion exchange according to the present invention.

FIG. 2 shows an embodiment of an ion exchange train (100) with cationic exchanger bed (102) and anionic exchanger bed (104) operated in series. A network of main process lines and utility lines used for flushing, regenerating, and rinsing, are also shown. In production mode, WCP stream (104) is directed to the inlet of the cation unit (106) and distributed across the top of the cation resin bed (102). The cation unit (106) is maintained in a flooded state by monitoring the level in the vent separator (108) through which non-condensables are purged to line (110).

The WCP stream (104) contacts the cation exchange resin bed (102) to remove sodium ions, which are exchanged for hydrogen or other cations. The cation exchange resin bed (102) can comprise either a strong-acid type or a weak-acid type resin. Strong-acid ion exchange resins typically have sulfonic acid functional groups, and representative examples are available commercially from Rohm & Haas under the trade designations Amberlyst® 15, Amberlyst® 35, Amberlyst® 36, and the like. Weak-acid ion exchange resins typically have carboxylic acid moieties, and representative examples are commercially available from Rohm & Haas under the trade designations Amberlite® IRC 76, Amberlite® IRC 84, and the like.

As WCP (104) passes through the cation unit (106), the cationic resin converts soluble salts to their corresponding acids, including phenol. For example, ion exchange interactions can proceed as follows:

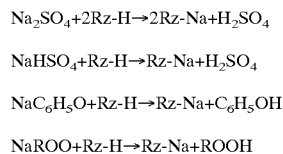

wherein "Rz" represents a moiety in the ion exchange medium, either acidic or basic, and "R" represents an organic radical in the WCP stream (104).

The acidic WCP effluent (112) then passes through the anion unit (114) containing anion exchange resin bed (104). The anion unit (114) is maintained in flooded state via vent separator (116) and non-condensables purge stream (118) in a manner similar to cation unit (106). Either a weakly or strongly basic exchange resin or a series of weakly and strongly basic exchange resins can be used. Weakly basic ion exchange resins typically have tertiary amine moieties; representative examples are available commercially from Rohm & Haas under the trade designations Amberlyst® A21, Amberlyst® A23, Amberlyst® A24, and the like. Strong anion exchange resins typically have quaternary ammonium ions; a representative example is commercially available from Rohm & Haas under the trade designation Amberlyst® A26 OH, and the like.

When a weakly basic exchanger is used, the mineral acid is removed according to the following reaction:

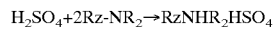

wherein "NR$_2$" represents an amine function on the weak base resin. When a strongly basic exchanger is used, both mineral and weakly acidic organic acids are removed. Initially the exchanger is converted from its hydroxide form to a phenolic form, and stronger organic acids then progressively replace the phenolic groups, followed by mineral acids:

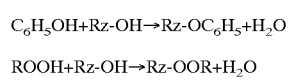

$$ROOH + Rz\text{-}OC_6H_5 \rightarrow Rz\text{-}OOR + C_6H_5OH$$

$$H_2SO_4 + 2Rz\text{-}OC_6H_5 \rightarrow Rz\text{—}SO + 2C_6H_5OH$$

$$H_2SO + 2Rz\text{-}OOR \rightarrow Rz_2\text{—}SO + 2ROOH$$

The effluent (120) from the anion exchanger (114) thus has a reduced acid content and is essentially neutralized relative to the feed (112) for acetone and phenol recovery. Downstream materials of construction are considered when specifying the anion unit (114).

When adsorptive capacity in an operating ion exchanger becomes saturated, the exchanger is taken off-line for regeneration. As a practical consideration, resin saturation in industrial plant operation can fall short of absolute saturation due to economic and operating issues that are determined on plant-specific bases. Criteria by which operating "saturation" is defined can include minimizing reagent consumption, minimizing organic waste production, controlling waste quality, optimizing plant maintenance turnaround cycles, or maximizing product purities, for example. To replace the exchanger entering regeneration, an exchanger waiting in standby (refer below to FIG. 4) will be placed in operation before isolating the exchanger to be regenerated from the manufacturing streams. This description assumes cationic and anionic exchangers (106), (114) will be regenerated in a shared cycle. It is also possible to regenerate cation and anion exchangers independently at different frequencies or intervals, depending on respective rates of capacity utilization.

Regeneration occurs in three stages, displacement, cation exchange resin regeneration, and anion exchange resin regeneration. WCP is first displaced from piping and vessels with nitrogen (122), flowing from the cation unit (106) through the anion unit (114), discharging to the product recovery line (120). The cation and anion units are de-pressured via the vent lines (110), (118). After displacement by nitrogen, residual liquid is recycled via lines (124), (126) to the cleavage product washing unit.

Displacement preferably includes "sweetening off" the exchangers, which entails passing at least two bed volumes of acetone or other solvent through the cation and anion exchangers (106), (114) while maintaining the beds (102), (104) in a flooded condition. Sweetening off promotes good wetting of the exchanger media by aqueous regenerant streams. The solvent-purged resin can then be contacted with water for subsequent regeneration steps without complications of forming multiple liquid phases.

The cation exchanger (106) is initially back-washed with cold condensate (128), for example at 15–30° C., discharging out of the top via line (130) to a phenolic water collection tank (132). The cation exchanger (106) is regenerated with sulfuric acid (134) diluted with cold condensate via line (136), which enters the top of the unit 106 via a distributor located above the exchanger bed (102) and discharges via line (138) to the tank (132). Acid regeneration is followed by acid displacement via cold condensate line (136), with discharge (138) to the tank (132). The cation exchanger (106) is then fast rinsed via cold condensate line (136), continuing the discharge (138) to the phenolic water tank (132). After the phenol content of the fast rinse water discharge (138) falls to an acceptable concentration, for example below 0.5 weight percent, the fast rinse water discharge is diverted via line (140) directly to wastewater treatment, which can include dephenolation. Fast rinse is stopped when an acceptable low conductivity level has been reached, for example 10–20 micromhos.

The anion exchanger (114) is initially back-washed with warm condensate via backwash line (142), for example at 30–50° C., with discharge via line (112) and discharge line (144) to the phenolic water collection tank (132). The anion exchanger (114) is regenerated with a distributor at the top using sodium hydroxide (caustic) solution (146) diluted with warm condensate via line (148), discharging via line (150) to the tank (132). Caustic regeneration is followed by displacement with warm condensate (148) and discharge (150) to the tank (132). The anion exchanger (114) is then fast-rinsed with cold condensate via lines (152), (112) and discharge (150) to the tank (132). When the phenol content of the fast rinse water falls to an acceptable concentration, for example below 0.5 weight percent, the fast rinse water is diverted via line (154) directly to wastewater treatment, which can include dephenolation. Fast rinse is stopped when an acceptable low conductivity has been reached, for example 10–20 micromhos.

After completing the cation and anion regeneration, the water is displaced with nitrogen (122) from the cation unit (106) through the anion unit (114), discharging via line (154) to wastewater treatment. The cation and anion units (106), (114) are de-pressured via vent lines (110), (118). Residual liquid is drained and recycled via lines (124), (126) to the cleavage product washing unit. The exchanger units (106), (114) are back-filled with polished WCP via line (156) and are left liquid-filled and off-line until needed for adsorption operation.

Figure 3:
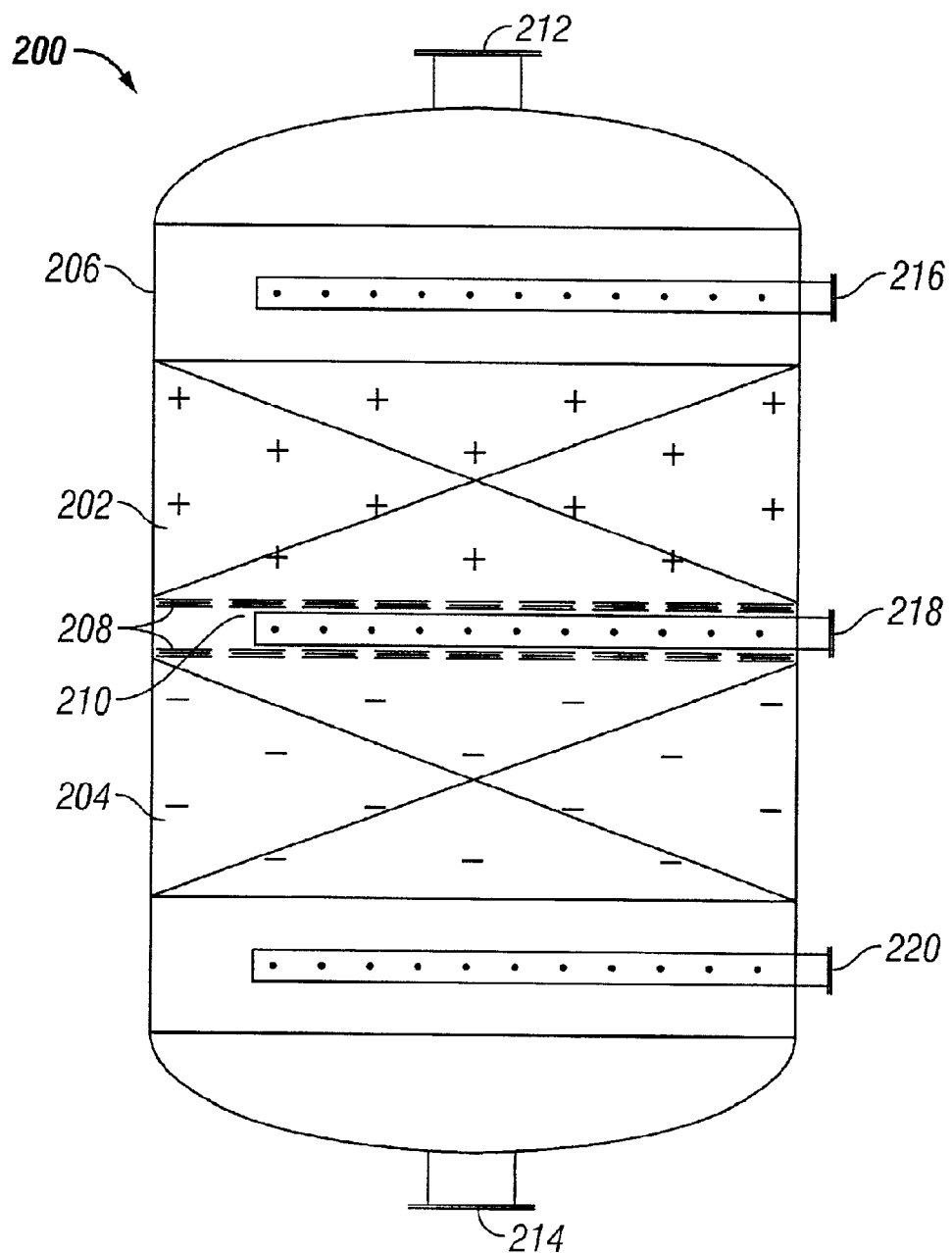
FIG. 3 is a simplified cross section showing an embodiment of an ion exchange contactor for installing both cationic and anionic resins in separate beds in one vessel.

A mixed-resin bed (200) is shown in FIG. 3, providing both a cation exchange bed (202) and an anion exchange bed (204) in a common vessel (206). Alternatively, the resins can comprise a heterogeneous mixture of each type of resin in a single bed (not shown). The resin beds (202), (204) are separated by a physical spacer such as perforated support plates (208) and/or a layer of inert resin (210). Upper main nozzle (212) and lower main nozzle (214) are used for ion removal by using nozzle (212) as an inlet and (214) as an outlet. Regeneration fluids can be introduced and removed at ports (216), (218), (220), as well as at the main nozzles (212), (214) for independent bed regeneration, which would proceed generally as described above. A representative compact bed system for mixed resins is commercially available from Rohm & Haas under the trade designation Amberpack®.

Figure 4:
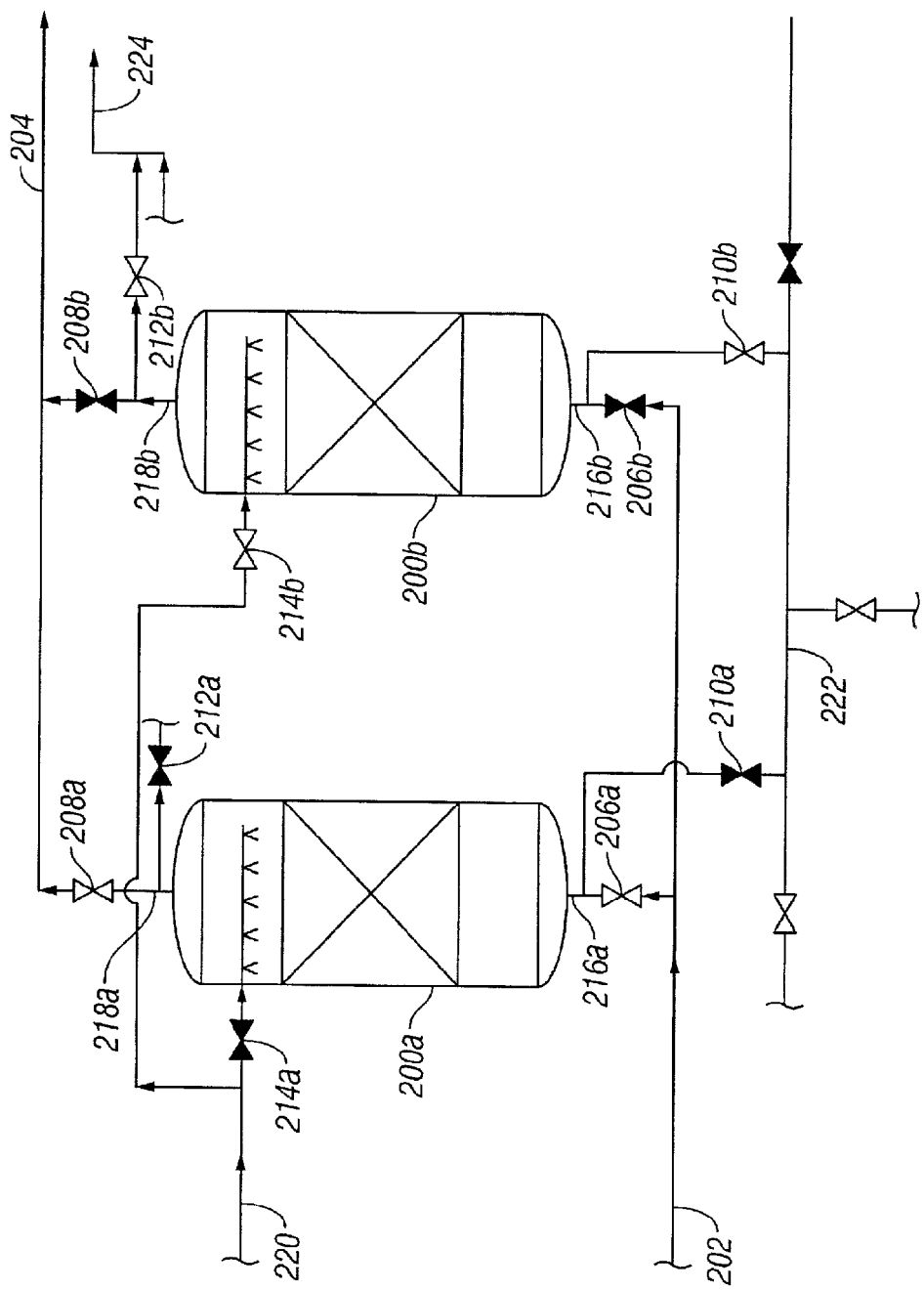
FIG. 4 is a simplified process flowsheet of an embodiment using an ion exchange resin bed in parallel configuration to enable continuous plant operation.

For continuous process operations in plants configured using either separate cationic/anionic exchanger beds or mixed-bed exchangers, at least two sets of ion exchanger units are preferred. In a two-set system, one exchanger set will be in adsorption service, while another set is in regeneration/standby status, and any additional sets are in standby status. FIG. 4 shows a pair of exchangers (200a), (200b) with WCP feed line (202) and polished WCP effluent line (204) configured for up-flow operation by selectively opening or closing valves (206a), (206b), (208a), (208b), (210a), (210b), (212a), (212b), (214a), (214b). If the solid-body valves (206b), (208b), (210a), (212a), (214a) are closed and the outline-body valves (206a), (208a), (210b), (212b), (214b) are open, the drawing shows exchanger (200a) in adsorption service and exchanger (200b) in regeneration.

Regeneration flows and discharges are provided through a piping network using the main vessel process inlet/outlet connections (216a), (216b), (218a), (218b). Line (220) introduces regenerant and flushing fluids via distributors for down-flow. Drainage and discharge use the header (222), which can also be used for the introduction of any upflow displacement and rinse streams in conjunction with vent header (224).

Metal ion removal from WCP, particularly of sodium ions, has various technical and commercial advantages.

Reducing the metal ion content of the WCP can increase the capacity of a phenol plant, typically by 5–10%, e.g. by increasing operating periods due to less frequent as well as shorter shutdowns for cleaning fouling deposits from heat transfer equipment in the distillation units. Ion removal from WCP can also lower utility costs by 5–10% at the same production rate, e.g. by reducing fouling in heat exchange networks in the product recovery system. The ion removal also removes salts that can form heavy-end organic byproducts, and thus reduces or eliminates the processing in heavy-end salt removal systems conventional in phenol plants, as well as heavy ends incineration and ash emissions.

EXAMPLE 1

Table 1 shows a composition of a simulated washed cleavage product synthesized for testing ion removal according to the present invention. Industrial phenol process systems, without coalescers, can produce a WCP with sodium levels in a range of about 25 to 30 parts per million by weight (ppmw). Higher values are not uncommon, however, and this case exhibits a sodium ion concentration of 61 ppmw. Coalescing can reduce sodium levels to 20 ppmw or slightly lower. The WCP composition in Table 1 exemplifies a potential WCP feed to an ion exchange unit. This composition was used in the testing reported below in Examples 2–3.

TABLE 1

Synthetic WCP Composition.

| WCP Component | Parts by Weight |
| --- | --- |
| Acetone | 33 |
| Cumene | 13 |
| Alpha-methylstyrene | 2 |
| Phenol | 42 |
| Water | 10 |
| NaOH | 0.010 |
| Acetic Acid | 0.010 |
| Formic Acid | 0.010 |
| Sodium Sulfate ($Na_2SO_4$) | 0.010 |
| Total | 100 |
| Sodium ion | 61 ppmw |
| Sulfate ion | 7 ppmw |

EXAMPLE 2

Four cationic exchanger resins were tested in a batch-mode stirred reactor to measure of resin capacities to adsorb sodium ion from WCP. The tests used cationic macroreticular resins based on sulfonated, crosslinked styrene-divinylbenzene copolymers. Typical properties for each are shown in Table 2.

TABLE 2

Cation Exchange Resins.

| Resin | Cation exchange capacity, eq/kg | Cation exchange capacity, eq/L | Moisture holding capacity, wt % |
| --- | --- | --- | --- |
| Cation C1 | 4.88 | 1.81 | 53.7 |
| Cation C2 | 5.08 | 1.76 | 55.8 |
| Cation C3 | 5.53 | 2.05 | 55.0 |
| Cation C4 | 5.29 | 2.23 | 48.9 |

Batch testing comprised stirring a 0.5 gram resin sample in 200 grams of synthetic washed cleavage product (see Example 1) containing about 61 ppmw of dissolved sodium. Four resin tests were run maintaining the solutions at a temperature of about 50° C. to prevent phase separation. Sodium ion concentrations were measured for samples taken at 15-minute intervals during a one-hour run. Table 3 lists the measured sodium ion concentrations at the tests sample intervals. The results show the four resins to have roughly equal adsorption capacities and differing adsorption rates.

TABLE 3

Sodium Adsorption from Synthetic WCP-Resin Mixtures.

| | Initial [$Na^+$] in WCP, | Final [$Na^+$] after Resin Addition, ppmw Time (minutes): | | | |
| --- | --- | --- | --- | --- | --- |
| Cation Resin | ppmw | 15 | 30 | 45 | 60 |
| Cation C1 | 56 | 41 | 36 | 33 | 13 |
| Cation C2 | 49 | 37 | 31 | 36 | 14 |
| Cation C3 | 57 | 16 | 18 | 14 | 13 |
| Cation C4 | 56 | 23 | 13 | 14 | 14 |

EXAMPLE 3

The ion exchange adsorption rates and capacities for sodium and sulfate in WCP were next determined in a continuous-flow column test using a two-bed exchanger unit for the resins of Example 2. The synthetic WCP of Example 1 was pumped through the two beds in series. The tests beds were fabricated using ½-inch diameter stainless steel tubing, and the beds were immersed in a thermostatically controlled oil bath to maintain operating temperatures at about 50° C. The first bed held the Cation C4 resin of Example 2, above, and the second bed used a gel-type acrylic weak-base anion exchange resin in free-base form (Anion A1). Corresponding to the cation resin properties reported in Table 2, above, the Anion A resin had a typical anion exchange capacity of 5.98 eq/kg and 1.66 eq/L, and a moisture holding capacity of 60 weight percent.

Sodium ion concentrations were measured in effluent samples from the second (anion) exchanger bed, collected at 4-hour intervals. Test conditions were maintained at 50° C., and the WCP flow rate was kept at 8 bed volumes per hour (BV/h). Based on the Cation C4 adsorption capacity reported in Table 1 and the WCP feed concentration of 61 ppmw sodium set in Example 1, above, it was estimated that the test column of this example had a theoretical capacity to treat 830 bed volumes of the synthetic WCP solution to complete sodium removal. The test lasted until rising effluent sodium concentration began to emerge in the effluent of the second-stage resin bed, measured at 780 and 820 bed volumes. Analyses are reported in Table 4. The data are reported at increments of cumulative WCP volume treated, reported in terms of bed volume (BV), defined as the empty-space volume occupied by the resin in the column.

TABLE 4

Column Flow Test with Synthetic WCP.

| WCP Treated, BVs | WCP Feed [$Na^+$], ppmw | WCP Effluent [$Na^+$] ppmw |
| --- | --- | --- |
| 200 | 69 | 0.3 |
| 600 | 65 | 0.3 |
| 820 | 64 | 7.8 |

The resin in each column was regenerated using regeneration flow rates about equal to the operating bed flow rate of 8 BV/h. Switching from the synthetic WCP feed, acetone solvent (neat) was pumped through the columns for 1 hour, followed by demineralized water for 1 hour. The cation bed was physically disconnected from the anion bed, and 6 BV (30 mL) of 1N $H_2SO_4$ was pumped through the cation bed, followed by approximately 24 BV demineralized water and 12 BV of acetone through the cation bed. Through the anion bed were pumped 3 BV (15 mL) of 1 Normal NaOH, followed by approximately 20 BV demineralized water and 12 BV of acetone. The cation bed was then connected to the anion bed and 8 BV of acetone pumped through the combined system. The feed was then switched to WCP for the next cycle of testing.

EXAMPLE 4

An additional series of tests were run with commercial WCP using a WCP flow rate of 37.5 BV/h. Fresh (new) resins were installed in the columns, using the Cation C4 and Anion A1. For this experiment, sample analyses were performed using ion-chromatography/mass spectrometry, indicating an average sodium concentration of 59 ppmw in the commercial WCP.

Three adsorption campaigns were run, and after each adsorption run the columns were regenerated using the protocol of Example 3. Subsequent adsorption cycles were run using the same flow conditions as the first cycle. The data for the adsorption series are shown in Table 5. The results show that sodium levels were consistently reduced to levels of about 10 ppmw or less through multiple cycles of resin loading and regeneration.

TABLE 5

Column Flow Test at 37.5 BV/h for 3 Cycles.

| WCP Treated, BVs | WCP Effluent [Na$^+$], ppmw | | |
|---|---|---|---|
| | Cycle 1 | Cycle 2 | Cycle 3 |
| 150 | <1 | 1 | 10 |
| 300 | <1 | 1 | 8 |
| 600 | 10 | 2 | 6 |

Sulfate ion content was also measured in the effluent. The results presented in Table 6 show a pronounced reduction in WCP sulfate concentrations paralleling the sodium ion concentrations.

TABLE 6

Effluent Sulfate from WCP Treatment.

| WCP Treated, BVs | WCP Effluent [SO4$^{-2}$], ppmw | | |
|---|---|---|---|
| | Cycle 1 | Cycle 2 | Cycle 3 |
| 280 | 0.1 | 0.2 | 12 |
| 580 | 3 | 14 | 3 |

The invention is described above with reference to non-limiting examples provided for illustrative purposes only. Various modifications and changes will become apparent to the skilled artisan in view thereof. It is intended that all such changes, modifications, and applications are within the scope and spirit of the appended claims and shall be embraced thereby.

What is claimed is:

1. A process for reducing ion content of washed cleavage product from the reaction of cumene hydroperoxide with an acid catalyst, comprising:

contacting the washed cleavage product with a cation exchanger to remove positively charged ions including sodium;

contacting the washed cleavage product with an anion exchanger to remove negatively charged ions including sulfate; and recovering exchanger effluent lean in sodium and sulfate.

2. The process of claim 1 wherein the washed cleavage product comprises whole washed cleavage product.

3. The process of claim 1 wherein the washed cleavage product comprises dewatered cleavage product.

4. The process of claim 1 wherein the washed cleavage product comprises:

a molar ratio of acetone to phenol from 0.8 to 1.5;
   from 2 to 30 weight percent cumene;
   from 4 to 20 weight percent water; and
   from 10 to 400 ppmw sodium.

5. The process of claim 1, wherein the cation exchanger comprises strong acid cation exchange resin in hydrogen form.

6. The process of claim 1, wherein the cation exchanger comprises weak acid cation exchange resin in hydrogen form.

7. The process of claim 1, wherein the anion exchanger comprises weak base anion exchange resin in free base form.

8. The process of claim 1, wherein the anion exchanger comprises strong base anion exchange resin in hydroxide form.

9. The process of claim 1, wherein the anion and cation exchanger contacting comprises passing the washed cleavage product through a mixed bed of exchanger media comprising both cation and anion exchangers.

10. The process of claim 9, wherein the effluent has a sodium concentration less than 10 ppmw.

11. The process of claim 1, wherein the cation and anion exchangers comprise serial beds of cation and anion exchange resins, respectively.

12. The process of claim 1, wherein the cation bed effluent has a sodium concentration less than 10 ppmw and a pH from 3.5 to 6.0.

13. The process of claim 1, comprising a cation exchange adsorption cycle at a temperature from 20° to 80° C. and a feed rate from 1 to 60 BV/h.

14. The process of claim 13, comprising a cation exchange regeneration cycle with from 0.5 to 10 weight percent aqueous sulfuric acid.

15. The process of claim 1, comprising an anion exchange adsorption cycle at a temperature from 20° to 80° C. and a feed rate from 1 to 60 BV/h.

16. The process of claim 15, comprising an anion exchange regeneration cycle with aqueous NaOH, sodium phenate, or a combination thereof, at NaOH or NaOH-equivalent concentration from 0.2 to 8 weight percent.

17. A process for producing phenol, comprising:

oxidizing cumene to cumene hydroperoxide;

cleaving the cumene hydroperoxide in the presence of an acid catalyst to form a cleavage product mixture including phenol and acetone;

washing the cleavage product mixture with alkaline wash solution to form a washed cleavage product;

contacting the washed cleavage product with a cation exchanger and an anion exchanger to form a polished cleavage product of reduced ion content; and recovering phenol and acetone from the polished cleavage product.

18. The process of claim 17, wherein the cation exchanger comprises cation ion exchange resins in hydrogen form selected from strong acid cation exchange resins and weak acid cation exchange resins, and the anion exchanger comprises anion exchanger resin selected from weak base anion exchange resins in free base form and strong base anion exchange resins in hydroxide form.

19. The process of claim 17 wherein the polished cleavage product comprises less than 10 ppmw sodium.

20. The process of claim 17, wherein the polished cleavage product comprises less than 2 ppmw sodium.

21. The process of claim 17, wherein the washed cleavage product comprises a molar ratio of acetone to phenol from 0.8 to 1.5, from 2 to 30 weight percent cumene, from 4 to 20 weight percent water, and from 10 to 400 ppmw sodium.

22. The process of claim 21, wherein the washing includes coalescing a whole washed cleavage product to dewater the washed cleavage product for the exchanger contacting.

23. The process of claim 21, wherein the product recovery includes distillation of the polished cleavage product and recovery of an aqueous stream, and the process further comprises recycling the aqueous stream to the washing step.

24. The process of claim 21, further comprising dephenolating spent wash water from the washing.

25. The process of claim 24, further comprising regenerating the cation and anion exchanger with aqueous and organic fluids, recycling spent aqueous fluid to the dephenolation, and recycling spent organic fluid to the cleavage product washing or the phenol and acetone recovery.

* * * * *